United States Patent [19]

Araki et al.

[11] Patent Number: 4,889,857
[45] Date of Patent: Dec. 26, 1989

[54] QUINOLONECARBOXYLIC ACID COMPOUNDS AND PHARMACEUTICAL USE THEREOF

[75] Inventors: Kazuhiko Araki; Tsuyoshi Kuroda, both of Oita; Satoru Uemori; Akihiko Moriguchi, both of Fukuoka; Yoshifumi Ikeda, Oita, all of Japan

[73] Assignee: Yoshitomi Pharmaceutical Industries, Ltd., Osaka, Japan

[21] Appl. No.: 250,634

[22] Filed: Sep. 29, 1988

[30] Foreign Application Priority Data

| Oct. 12, 1987 | [JP] | Japan | 62-256779 |
| Nov. 20, 1987 | [JP] | Japan | 62-294759 |
| Jan. 28, 1988 | [JP] | Japan | 63-19352 |
| Jun. 3, 1988 | [JP] | Japan | 63-137909 |
| Aug. 17, 1988 | [JP] | Japan | 63-204004 |

[51] Int. Cl.$^4$ ............... A61K 31/535; C07D 413/04
[52] U.S. Cl. ............... 514/235.2; 514/222.2; 514/232.5; 544/58.6; 544/82; 544/121; 544/128
[58] Field of Search ............... 544/128, 121, 82, 58.6; 514/232.5, 235.2, 222.2

[56] References Cited

U.S. PATENT DOCUMENTS

| 4,382,892 | 5/1983 | Hayakawa et al. | 544/73 |
| 4,556,658 | 12/1985 | Grohe et al. | 544/128 |
| 4,665,079 | 5/1987 | Culbertson et al. | 544/363 |
| 4,670,444 | 6/1987 | Grohe et al. | 544/128 |
| 4,705,788 | 11/1987 | Schriewer et al. | 544/128 |
| 4,753,925 | 6/1988 | Grohe et al. | 544/128 |

*Primary Examiner*—Glennon H. Hollrah
*Assistant Examiner*—James H. Turnipseed

*Attorney, Agent, or Firm*—Sughrue, Mion, Zinn, Macpeak & Seas

[57] ABSTRACT

A quinolonecarboxylic acid compound of the formula:

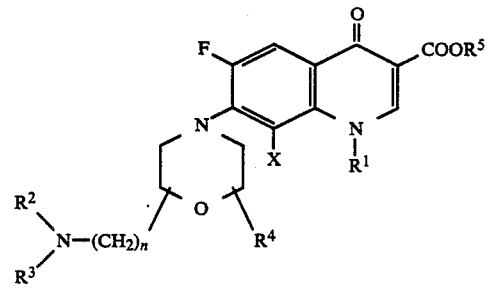

wherein $R^1$ is an alkyl group, a cycloalkyl group, a haloalkyl group, an alkenyl group, mono- or di-alkylamino groups, a phenyl group or a phenyl group substituted by one to three substituents selected from the group consisting of a halogen atom, an alkyl group, an alkoxy group, a hydroxy group, a nitro group or an amino group, $R^2$ is a hydrogen atom, an alkyl group, a cycloalkyl group, an acyl group or an alkoxycarbonyl group, $R^3$ is a hydrogen atom, an alkyl group or an aralkyl group, or $R^2$ and $R^3$ together with the adjacent nitrogen atom form a heterocyclic ring, $R^4$ is a hydrogen atom or an alkyl group, $R^5$ is a hydrogen atom, an alkyl group, an aralkyl group or an ester residue which is readily hydrolyzable in vivo, X is a hydrogen atom, a halogen atom or an alkyl group, n is interger of 1 to 3, and a salt thereof, and pharmaceutical use thereof.

The compounds exhibit antibacterial activites and are useful for the treatment of various infectious diseases.

5 Claims, No Drawings

QUINOLONECARBOXYLIC ACID COMPOUNDS AND PHARMACEUTICAL USE THEREOF

BACKGROUND OF THE INVENTION

The present invention relates to novel and pharmaceutically useful quinolonecarboxylic acid compounds having more potent antibacterial activities and salts thereof, and pharmaceutical uses thereof.

As antimicrobial fluorinated quinolonecarboxylic acids, 1-ethyl-6-fluoro-1,4-dihydro-7-(1-piperazinyl)-4-oxoquinoline-3-carboxylic acid (norfloxacin, U.S. Pat. No. 4,146,719) 9-fluoro-3-methyl-10-(4methyl -1- piperazinyl)-7-oxo-2,3-dihydro-7H-pyrido [1,2,3-de][1,4]-benzoxazine-6-carboxylic acid (ofloxacin, U.S. Pat. No. 4,382,892) and 1-cyclopropyl-6-fluoro-1,4-dihydro-7-(1-piperazinyl)-4-oxoquinoline-3-carboxylic acid (ciprofloxacin, U.S. Pat. No. 4,620,007) are exemplified.

Though the foregoing quinolonecarboxylic acid compounds have broad antibacterial activities against both gram-positive and gram-negative bacteria, their antibacterial activities are not as effective against gram-positive as against gram-negative bacteria. It has recently become a clinical problem that infections caused by gram-positive bacteria are increasing because the bacteria are refractory to chemotherapy. These bacteria include Staphylococcus such as methycillin.cephemresistant Staphylococcus aureus having hyper-resistance to β-lactam antibiotics, especially the third generation-cephem compounds or Staphylococcus epidermidis, Enterococcus and Streptococcus such as Streptococcus pyogenes. Therefore, it has been desired to provide antibacterial agents which possess more potent antibacterial activities not only against gram-negative bacteria, but also against gram-positive bacteria and do not cause microbial substitution. Moreover, it is desirable to develop antibacterial agents with enhanced bactericidal activities compared to the pyridonecarboxylic acid compounds currently used in the treatment of bacterial infections against immunosuppression-affected patients by basal disease and so on. Therefore, various intensive research is underway in an effort to improve or enhance the spectrum of activity.

SUMMARY OF THE INVENTION

The present invention provides a new series of quinolonecarboxylic acid compounds which possessing enhanced potent and broader antibacterial activities in vitro and in vivo against gram-positive bacteria as well as against gram-negative bacteria in comparison with the conventional pyridonecarboxylic acid compounds, having better absorption by oral administration with less serious side effects and low toxicity, and a pharmaceutical use thereof.

DETAILED DESCRIPTION OF THE INVENTION

The present invention relates to quinolonecarboxylic acid compounds of the formula:

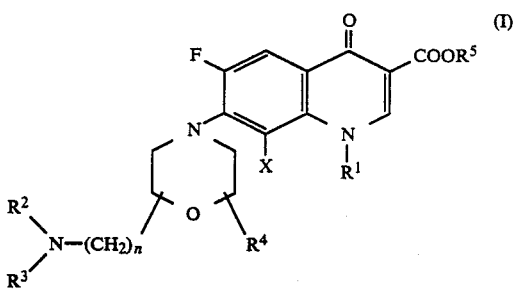

wherein $R^1$ is an alkyl group, a cycloalkyl group, a haloalkyl group, an alkenyl group, mono- or dialkylamino groups, a phenyl group or a phenyl group substituted by one to three substituents selected from the group consisting of a halogen atom, an alkyl group, an alkoxy group, a hydroxy group, a nitro group or an amino group, $R^2$ is a hydrogen atom, an alkyl group, a cycloalkyl group, an acyl group or an alkoxycarbonyl group, $R^3$ is a hydrogen atom, an alkyl group or an aralkyl group, or $R^2$ and $R^3$ together with the adjacent nitrogen atom form a heterocyclic ring, $R^4$ is a hydrogen atom or an alkyl group, $R^5$ is a hydrogen atom, an alkyl group, an aralkyl group or an ester residue which is readily hydrolyzable in vivo, X is a hydrogen atom, a halogen atom or an alkyl group, n is integer of 1 to 3, and a salt thereof, and a pharmaceutical use thereof.

In the difinitions of the above symbols, the halogen atom means chlorine, bromine, fluorine and iodine; the alkyl group means alkyl having 1 to 18 carbon atoms such as methyl, ethyl, propyl, isopropyl, butyl, isobutyl, tert-butyl, pentyl, hexyl, heptyl, octyl, decyl, dodecyl or octadecyl; the alkoxy group means alkoxy having 1 to 18 carbon atoms such as methoxy, ethoxy, propoxy, isopropoxy, butoxy, isobutoxy, tert-butoxy, pentyloxy, hexyloxy, octyloxy, decyloxy, dodecyloxy or octadecyloxy; the alkenyl group means alkenyl having 2 to 8 carbon atoms such as vinyl, allyl, butenyl, pentenyl, hexenyl and octenyl; the haloalkyl group means alkyl group having 1 to 8 carbon atoms substituted by at least one halogen atom includes difluoromethyl, trifluoromethyl, fluoroethyl or trifluoroethyl; the mono- or dialkylamino group means amino substituted by one or two alkyl groups having 1 to 8 carbon atoms each, and includes methylamino, ethylamino, propylamino, isopropylamino, butylamino, tert-butylamino, hexylamino, octylamino, dimethylamino, diethylamino, dipropylamino, diisopropylamino, dibutylamino, dihexylamino or dioctylamino; the cycloalkyl means cycloalkyl having 3 to 7 carbon atoms such as cyclopropyl, cyclobutyl, cyclopentyl, cyclohexyl and cycloheptyl; the acyl group means acyl having 1 to 5 carbon atoms such as formyl, acetyl, propionyl, butyryl, valeryl and pivaloyl; the alkoxycarbonyl group in which the alkoxy moiety bears 1 to 4 carbon atoms includes methoxycarbonyl, ethoxycarbonyl, propoxycarbonyl, isopropoxycarbonyl, butoxycarbonyl, isobutoxycarbonyl or tert-butoxycarbonyl inclusive of benzyloxycarbonyl, the aralkyl group means aralkyl which may be optionally substituted on the benzene ring by 1 to 3 substituents selected from a halogen atom, an alkyl group, an alkoxy group, a trifluoromethyl group, a hydroxy group, a nitro group or an amino group such as benzyl, o-, m- or p-chlorobenzyl, o-, m- or p-methylbenzyl, o-, m- or p-methoxybenzyl, o-, m- or p- trifluoromethylbenzyl, o-, m-or p-hydroxybenzyl, o-, m- or p-nitrobenzyl or o-, m- or p-aminobenzyl, phenylethyl, phenylpropyl, phenylbutyl and naphylmethyl; the heterocyclic ring formed by $R^2$ and $R^3$ together with the adjacent nitrogen atom means a 5 to 7-membered heterocyclic ring having at least one nitrogen atom such as pyrrolizine, piperidine, morpholine, thiomorpholine, piperazine and 4-methylpiperazine; the ester residue which is readily hydrolyzable in vivo, may be easily decomposed to free carboxylic acid and its salt in vivo includes, for example, an alkanoyloxyalkyl ester such as acetoxymethyl ester, pivaloyloxymethyl ester, 1-acetoxyethyl ester or 1-pivaloyloxyethyl ester, an alkoxycarbonyloxyalkyl ester such as ethoxycarbonyloxymethyl ester or 1-ethoxycarbonyloxyethyl ester, an ester such as phthalidyl or dimethoxyphthalidyl, a carbamoylalkyl ester such as carbamoylmethyl ester, carbamoylethyl ester, N-methylcarbamoyl methyl ester, N,N-dimethylcarbamoylmethyl ester, N,N-diethylcarbamoylmethyl ester, an alkoxyalkyl ester such as methoxymethyl ester or methoxyethyl ester, and 5-methyl-2-oxo-1,3-dioxolen-4-ylmethyl ester.

The salts of the compounds of formula (I) according to the present invention exist as an acid addition salt or a salt with a metal. The acid addition salt includes, for example, salts with inorganic acids such as hydrochloric, sulfuric and phosphoric acids, and salts with organic acids such as methanesulfonic, p-toluenesulfonic, lactic, acetic, citric and tartaric acids. The salt with a metal includes, for example, salts with an alkali metal and an alkaline earth metal (e.g. sodium, potassium, calcium and magnesium), or salts with a heavy metal such as copper, zinc, iron, gold, silver, platinum and manganese.

The present invention also embraces the corresponding hydrate forms (e.g. monohydrate, hemihydrate or sesquihydrate) or other solvate forms of the compounds of formula (I).

The compounds of formula (I) contain 1 to 2 asymmetric carbon atoms with respect to the morpholine group on the 7-position of the quinolone nucleus. Therefore, the compounds of formula (I) are present in the form of optical isomers or stereoisomers on the basis of the asymmetric carbon atom(s). The present invention, of course, includes all classes of these individual isomers and the mixture thereof.

The preferable compounds of the present invention are the compounds selected from the group consisting of 1-cyclopropyl-6,8-difluoro-1,4-dihydro-7-[2-(methylaminomethyl)morpholino]-4-oxoquinoline-3-carboxylic acid, 1-cyclopropyl-6,8-difluoro-1,4-dihydro-7-[2-(dimethylaminomethyl)morpholino]-4-oxo-quinoline-3-carboxylic acid, 7-[2-(aminomethyl)morpholino]-1-cyclopropyl-6,8-difluoro-1,4-dihydro-4-oxoquinoline-3-carboxylic acid, 1-cyclopropyl-7-[2-(ethylaminomethyl)morpholino]-6,8-difluoro-1,4-dihydro-4-oxoquinoline-3-carboxylic acid, 1-cyclopropyl-7-[2-(diethylaminomethyl)morpholino]-6,8-difluoro-1,4-dihydro-4-oxoquinoline-3-carboxylic acid, 7-[2-(acetylaminomethyl)morpholino]-1-cyclopropyl-6,8-difluoro-1,4-dihydro-4-oxoquinoline-3-carboxylic acid, 1-cyclopropyl-6,8-difluoro-7-[2-(formylaminomethyl)morpholino]-1,4-dihydro-4-oxoquinoline-3-carboxylic acid, 1-cyclopropyl-6,8-difluoro-1,4-dihydro-7-[2-(morpholinomethyl)morpholino]-4-oxoquinoline-3-carboxylic acid and 1-cyclopropyl-7-[2-(cyclopropylaminomethyl)morpholino]-6,8-difluoro-1,4-dihydro-4-oxoquinoline-3-carboxylic acid.

According to the present invention, the compounds of formula (I) can be prepared by the following methods:

METHOD 1

A method which comprises condensing a compound of the formula:

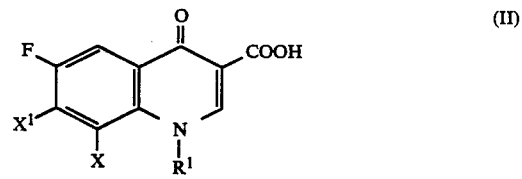

wherein $X^1$ is a halogen atom and other symbols are as defined above, with a compound of the formula:

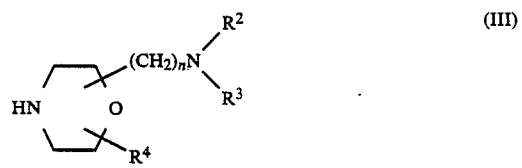

wherein each symbol is as defined above.

The condensation reaction is preferably carried out by using the compounds of formula (III) at the ratio of one to eight times molar of the compounds of formula (II) at 0°–200° C., preferably under heating 30°–150° C. for 1–48 hours without a solvent or, preferably in a suitable solvent. The suitable solvent includes, for example, water, an alcohol (e.g. methanol, ethanol or propanol), acetonitrile, pyridine, dimethylformamide, dimethyl sulfoxide, hexamethylphosphoric amide and 1-methyl-2-pyrrolidone. In this reaction, an organic base such as 1,8-diazabicyclo[5.4.0]undec-7-ene or triethylamine and an inorganic base such as potassium carbonate, sodium carbonate, potassium hydrogen carbonate or sodium hydrogen carbonate can be used as an acid scavenger.

The compounds of formula (II) can be synthesized by the methods as described in U.S. Pat. No. 4556658, Chem. Pharm. Bull., Vol. 32, p.4907, 1984 or J. Med. Chem., Vol. 30, p.504, 1987.

Other starting compounds of the formula (III), especially the compounds of formula:

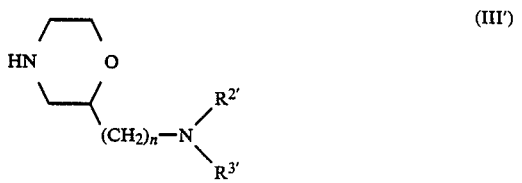

wherein $R^{2'}$, $R^{3'}$ are a hydrogen atom or an alkyl group, or $R^{2'}$ and $R^{3'}$ together with the adjacent nitrogen atom form a heterocyclic ring and the definitions of $R^2$ and $R^3$, n is as defined above, are novel compounds and can be, for example, prepared by aminating a morpholine compound of the formula:

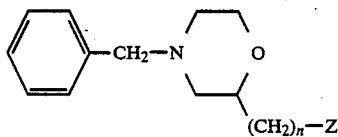

(IV)

wherein Z is an acid residue of an active esters (e.g. a halogen atom such as chlorine, bromine and iodine, -SO₄H, methanesulfonyloxy or p-toluenesulfonyloxy), and n is as defined above, with a compound of the formula:

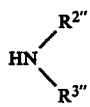

(V)

wherein R²″, R³″ are a hydrogen atom, an alkyl group or a benzyl group, or R²″ and R³″ together with the adjacent nitrogen atom form heterocyclic ring and the definitions of R² and R³, n is as defined above, and debenzylating the obtained morpholine compound of formula:

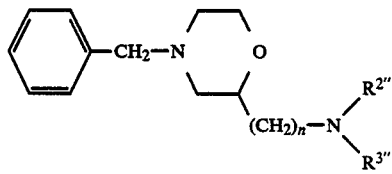

(VI)

wherein each symbol is as defined above.

The amination reaction is preferably carried out by using the compounds of formula (V) at the ratio of one to eight times molar of the compounds of formula (IV) at a temperature of room temperature to 150° C., for 1–48 hours without a solvent or in a suitable solvent. The suitable solvent includes water, an alcohol (e.g. methanol, ethanol, propanol or butanol), a ketone (e.g. acetone, or methyl ethyl ketone), an aromatic hydrocarbon (e.g. benzene, toluene or xylene), a halogenated hydrocarbon (e.g. chloroform, dichloromethane or dichloroethane), an ether (e.g. tetrahydrofuran, dioxane or diethyl ether), acetonitrile, pyridine, dimethylformamide, dimethyl sulfoxide, hexamethylphosphoric amide or 1-methyl-2-pyrrolidone. In this reaction, an organic base such as 1,8-diazabicyclo[5.4.0]undec-7-en or triethylamine, or an inorganic base such as sodium carbonate, potassium carbonate, sodium hydrogen carbonate or potassium hydrogen carbonate can be used as an acid scavenger. Further, a catalyst such as sodium iodine or potassium iodine can be used, if desired.

Furthermore, when the compound of formula (V) is ammonia, the compounds of formula (VI) wherein both R²″ and R³″ are hydrogen atoms can be obtained by the reaction in an autoclave.

The starting compounds of formula (IV) wherein n is an integer of 1 can be prepared by the method as described in Synthetic Communications, Vol. 10(1), p.59, 1980. The compounds of formula (IV) wherein n is an integer of 2 or more are novel and, for example, can be obtained by reducing ethyl 4-benzyl-2-morpholinylacetate and then converting the alcoholic hydroxyl group of 2-(4-benzyl-2-morpholinyl)ethanol thus obtained into the corresponding active ester group.

The compounds of formula (VI) wherein R²″ and R³″ are hydrogen atoms can be prepared by reacting a compound of the formula (IV) with potassium phthalimide, preferably in dimethylformamide, and then reacting the corresponding phthalimido compound with hydrazine hydrate, preferably in ethanol.

The debenzylation reaction is usually carried out at a temperature of room temperature to 150° C. and at ordinary atmospheric pressure to 100 atmospheres. A solvent such as water, an alcohol, acetic acid or a mixtures thereof, and a catalyst such as palladium-carbon, platinum oxide or Raney nickel can be used.

The compounds of formula (III″) wherein one of R²′ and R³′ is a hydrogen atom or an alkyl group, and the other of R²′ and R³′ is an alkyl group, can be prepared by reacting the compounds of formula (VI) wherein one of R²″ and R³″ is a benzyl group or an alykly group, and the other of R²″ and R³″ is an alkyl group, at the ratio of two to five times molar of a lower alkyl halocarbonate in a solvent such as benzene, toluene, xylene, chloroform or acetone, and then hydrolyzing with an alkali hydroxide such as sodium hydroxide or potassium hydroxide, or hydrobromic acid-acetic acid, or concentrated hydrochloric acid in an alcohol.

The compounds of formula (III″), if desired, can be used as the corresponding salts with an inorganic acid such as hydrochloric, hydrobromic, sulfuric or phosphoric acid, or an organic acid such as methanesulfonic, p-toluenesulfonic, lactic, acetic, citric or tartaric acid in a conventional manner.

METHOD 2

A method which comprises condensing a compound of the formula:

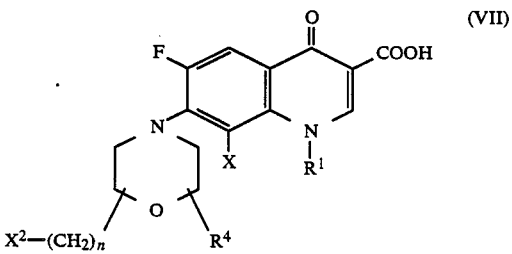

(VII)

wherein X² is a halogen atom and other symbols are as defined above, with a compound of the formula:

(VIII)

wherein each symbol is as defined above.

The condensation reaction is usually carried out by using the compounds of formula (VII) at the ratio of one to three times molar of the compounds of formula (VIII) at 0°–200° C., preferably under heating 100°–200° C. for 1–48 hours without a solvent or preferably in a suitable solvent. The suitable solvent is, for example, water, an alcohol, dimethylformamide, dimethyl sulfoxide or hexamethylphosphoric amide. In this reaction, sodium iodine or potassium iodine or the like can be used in order to accelerate the reaction.

The starting compounds of formula (VII) are new compounds and, for example, can be prepared by reacting a compound of the formula (II) with an amine compound of the formula:

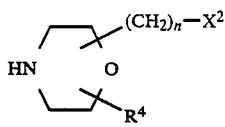

wherein each symbol is as defined above.

The reaction is preferably carried out by using the compounds of formula (II) at the ratio of one to eight times molar of the compounds of formula (IX) at 0°–200° C., preferably 30°–150° C. for 1–48 hours without a solvent or preferably in a suitable solvent. The suitable solvent includes water, an alcohol, acetonitrile, pyridine, dimethylformamide, dimethyl sulfoxide, hexamethylphosphoric amide or 1-methyl-2-pyrrolidone. In the reaction, usable acid scavengers include an organic base such as 1,8-diazabicyclo[5.4.0]undec-7-ene or triethylamine, or an inorganic base such as potassium carbonate, sodium carbonate, potassium hydrogen carbonate or sodium hydrogen carbonate.

METHOD 3

The compounds of formula (I) wherein $R^5$ is an alkyl group or an aralkyl group, can be converted into the corresponding carboxylic acid compounds of formula (I) wherein $R^5$ is a hydrogen atom by deblocking such protective group in a conventional manner.

The reaction can be carried out by hydrolysis or catalytic reduction in an acid or an alkali.

The compounds of formula (I) wherein $R^2$ is an acyl group, an alkoxycarbonyl group (e.g. ethoxycarbonyl, tertbutoxycarbonyl or benzyloxycarbonyl) and $R^3$ is a hydrogen atom, an alkyl group, or $R^2$ is a hydrogen atom and $R^3$ is an aralkyl group respectively, can be converted into the compounds of formula:

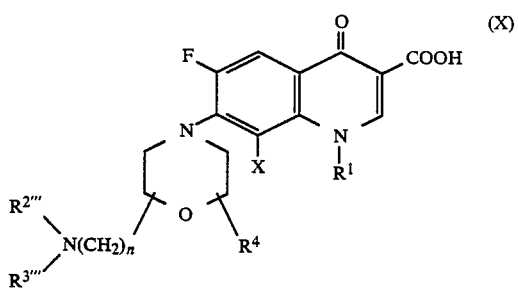

wherein $R^{2'''}$ is a hydrogen atom, $R^{3'''}$ is a hydrogen atom or an alkyl group in the definitions of $R^2$ and $R^3$, and other symbols are as defined above, by deblocking the protective group in such a conventional manner as hydrolysis or catalytic reduction in the presence of an acid or an alkali.

METHOD 4

A method which comprises cyclizing a compound of the formula:

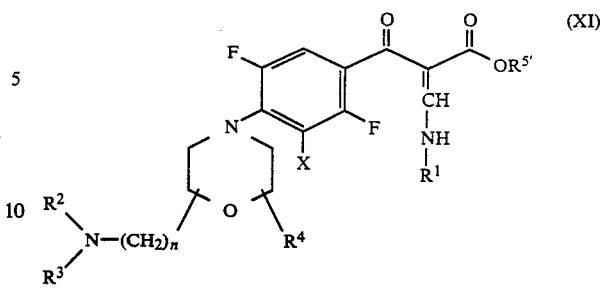

wherein $R^{5'}$ is an alkyl group or an aralkyl group in the definitions of $R^5$ and other symbols are as defined above, and, if desired, subjecting the thus obtained compound of the formula:

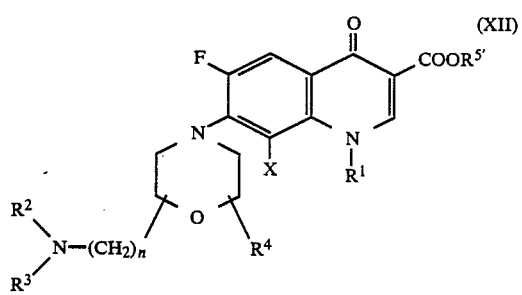

wherein each symbol is as defined above, to hydrolysis.

The cyclization reaction is usually carried out at 0° to 200° C., preferably under heating 50°–150° C. for 1 to several hours in the presence of a suitable base catalyst (e.g. sodium carbonate, potassium carbonate or 1,8-diazabicyclo[5.4.0]undec-7-ene) in, for example, a polar solvent such as dioxane, an alcohol (e.g. methanol, ethanol, propanol or butanol), dimethylformamide, dimethyl sulfoxide or tetrahydrothiophene 1,1-dioxide (sulfolane) and then hydrolyzing under an acid or base condition.

The starting compounds of formula (XI) are novel compounds and can, for example, be prepared by reacting a compound of the formula:

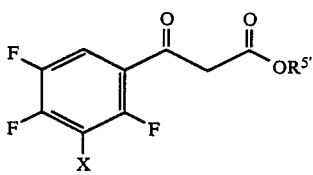

wherein each symbol is as defined above, with the compounds of formula (III) at 0°–200° C., preferably under heating at 50°–150° C. for several hours in a suitable solvent (e.g. acetonitrile, dimethylformamide, dimethylacetamide or dimethyl sulfoxide), if desired, in the presence of a base (e.g. sodium hydrogen carbonate, potassium hydrogen carbonate, sodium carbonate, potassium carbonate, triethylamine or 1,8-diazabicyclo[5.4.0]-undec-7-ene), reacting the thus obtained compound of the formula:

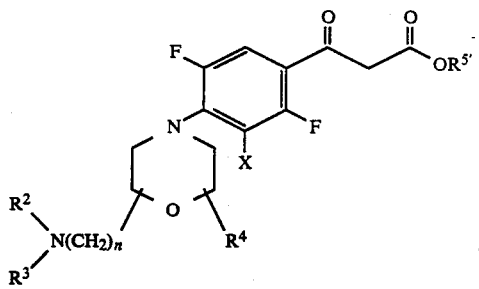 (XIV)

wherein each symbol is as defined above, with an ortho-formic ester and a glacial acetic anhydride, or a dimethylformamide dialkylacetal (e.g. dimethylformamide dimethylacetal or dimethylformamide diethylacetal), and then reacting the resultant compound with a compound of the formula:

R¹-NH₂  (XV)

wherein R¹ is as defined above.

The compounds of formula (XIV) can also be prepared by reacting a compound of the formula:

 (XVI)

wherein each symbol is as defined above, with the compound of formula (III) at 0°–200° C., preferably under heating at 50°–150° C. for several hours in a suitable solvent (e.g. acetonitrile, dimethylformamide, dimethylacetamide or dimethyl sulfoxide), if desired, in the presence of a base (e.g. sodium hydrogen carbonate, potassium hydrogen carbonate, sodium carbonate, potassium carbonate, triethylamine or 1,8-diazabicyclo[5.4.0]undec-7-ene), hydrolyzing a obtained compound of the formula:

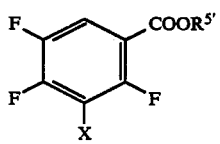 (XVII)

wherein each symbol is as defined above, with an acid or an alkali, reacting the obtained carboxylic acid compound with thionyl chloride, reacting the obtained acid chloride compound with magnesium ethoxide and diethylmalonate at −50° C. to 100° C., preferably −30° C. to 40° C. for several hours in a suitable solvent (e.g. toluene, benzene or xylene) and then reacting obtained compound of the formula:

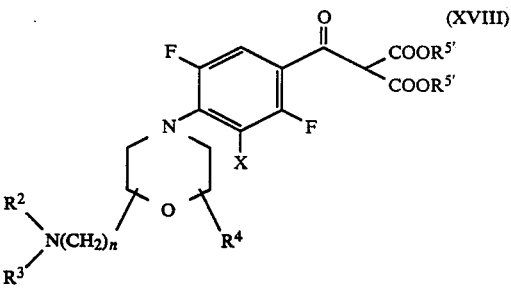 (XVIII)

wherein each symbol is as defined above, under heating at 50°– 150° C., preferably 50°–80° C. for several hours in the presence of a small amount of p-toluenesulfonic acid in an aqueous solvent.

The compounds of formula (XVIII) can also be prepared by reacting a compound of the formula:

 (XIX)

wherein each symbol is as defined above, with the compounds of formula (III).

The reaction is usually, carried out at 0°–200° C., preferably, under heating at 50°–150° C. for several hours in the presence of a suitable base (e.g. sodium hydrogen carbonate, potassium hydrogen carbonate, sodium carbonate, potassium carbonate, triethylamine or 1,8-diazabicyclo[5.4.0]undec-7- ene) in a suitable solvent (e.g. acetonitrile, dimethylformamide, dimethylacetamide or dimethyl sulfoxide).

The corresponding ester compounds of formula (I) which are readily hydrolyzable in vivo can be prepared by reacting the compound of formula (I) wherein R⁵ is a hydrogen atom, with a compound of the formula:

R⁵″-X³  (XX)

wherein R⁵″ is a ester residue which is readily hydrolyzable in vivo in the definitions of R⁵ and X³ is a halogen atom.

The carboxylic acid compounds of formula (I) can also be converted into the corresponding salts such as acid addition salts and metal salts, hydrates, alkyl esters and aralkyl esters as exemplified above in a conventional manner.

Usefulness of the compounds of the present invention as antibacterial agent has been demonstrated by the following experiments.

The test compounds employed are as follows:
Compound A : 1-cyclopropyl-6,8-difluoro-1,4,-dihydro-7-[2-(methylaminomethyl)morpholino]-4-oxoquinoline-3-carboxylic acid (Compound of the present invention)

Ofloxacin : 9-fluoro-3-methyl-10-(4-methyl-1-piperazinyl)-7-oxo-2,3-dihydro-7H-pyrido[1,2,3-de][1,4]-benzoxazine-6-carboxylic acid (OFLX, Compound for comparison)

Ciprofloxacin : 1-cyclopropyl-6-fluoro-1,4-dihydro-7-(1-piperazinyl)-4-oxoquinoline-3-carboxylic acid (CPFX, Compound for comparison)

EXPERIMENT 1 : Antibacterial activity (in vitro)

The antibacterial activities in vitro (minimum inhibitory concentration, MIC, μg/ml) of the test compounds were measured according to the standard method of the Japanese Chemotherapy Society (Chemotherapy, Vol. 23, p.1126, 1974). The results of antibacterial spectrum are shown in Table 1.

TABLE 1

| Organisms | MIC (μg/ml) | | |
|---|---|---|---|
| | Compound A | OFLX | CPFX |
| Staphylococcus aureus FDA 209P | 0.025 | 0.20 | 0.20 |
| Staphylococcus aureus FDA 209P* | 0.025 | 0.20 | 0.20 |
| Staphylococcus aureus 308A-1 | 0.05 | 0.39 | 0.39 |
| Staphylococcus aureus 1840 | 0.10 | 1.56 | 3.13 |
| Staphylococcus epidermidis ATCC 12228* | 0.05 | 0.20 | 0.20 |
| Staphylococcus epidermidis ATCC 12983* | 0.05 | 0.39 | 0.39 |
| Streptococcus pyogenes E-14* | 0.10 | 0.78 | 0.39 |
| Streptococcus pyogenes S-8* | 0.10 | 0.78 | 0.39 |
| Streptococcus viridans America* | 0.20 | 1.56 | 3.13 |
| Enterococcus faecalis LS-101* | 0.10 | 0.78 | 0.39 |
| Streptoccus pneumoniae Type 1* | 0.05 | 0.78 | 0.39 |
| Streptococcus sarivaris IFO 13956* | 0.20 | 3.13 | 1.56 |
| Streptococcus lactis IFO 12546* | 1.56 | 6.25 | 3.13 |
| Streptococcus sp. IFO 3535* | 1.56 | 3.13 | 3.13 |
| Corynebacterium diphtheriae Tronto* | 0.025 | 0.20 | 0.10 |
| Bacillus subtilis PCT 219 | 0.012 | 0.05 | 0.025 |
| Aerococcus viridans IFO 12219* | 0.10 | 3.13 | 0.78 |
| Pediococcus damnosus IFO 3895* | 0.39 | 0.20 | 0.10 |
| Micrococcus luteus IFO 12708* | 0.39 | 3.13 | 1.56 |
| Escherichia coli NIHJ JC-2 | 0.10 | 0.10 | 0.025 |
| Escherichia coli O-111 | 0.20 | 0.05 | 0.012 |
| Escherichia coli T-7 | 0.10 | 0.05 | 0.012 |
| Shigella typhosa Boxhill-58 | 0.05 | 0.025 | ≦0.006 |
| Shigella flexneri EW-10 | 0.025 | 0.05 | 0.012 |
| Shigella sonnei EW-33 | 0.025 | 0.025 | ≦0.006 |
| Klebsiella pneumoniae DT | 0.20 | 0.10 | 0.025 |
| Proteus vulgaris IFO 3988 | 0.78 | 0.10 | 0.05 |
| Morganella morganii IFO 3168 | 1.56 | 0.10 | 0.025 |
| Proteus mirabilis IFO 3849 | 1.56 | 0.39 | 0.10 |
| Serratia marcescens IFO 12648 | 0.78 | 0.20 | 0.10 |
| Acinetobacter calcoaceticus ATCC 13006 | 0.39 | 0.20 | 0.10 |
| Aerobacter aerogenes IFO 12979 | 0.20 | 1.56 | 0.78 |
| Alcaligenes faecalis NCTC 415 | 1.56 | 0.78 | 0.78 |
| Citrobacter freundii IFO 12681 | 0.20 | 0.05 | 0.012 |
| Enterobacter cloacae IFO 12937 | 0.78 | 0.39 | 0.10 |
| Flavobacterium meningosepticum IFO 12535 | 1.56 | 0.78 | 0.78 |
| Pseudomonas aeruginosa U-31 | 1.56 | 0.78 | 0.20 |
| Pseudomonas aeruginosa IFO 12582 | 3.13 | 1.56 | 0.20 |
| Pseudomonas cepacia 739 | 1.56 | 0.78 | 0.39 |
| Xanthomonas maltophilia IFO 12690 | 0.10 | 0.05 | 0.05 |

TABLE 1-continued

| Organisms | MIC (μg/ml) | | |
|---|---|---|---|
| | Compound A | OFLX | CPFX |
| Pseudomonas putida IFO 12996 | 1.56 | 1.56 | 0.10 |

(Inoculum size: $10^6$ cells/ml, Organisms with asterisk (*) were cultivated in a 10% horse blood-added medium.)

EXPERIMENT 2 : Protective effect against experimental infection in mice

Experimental infection was caused by inoculating male mice intraperitoneally with each organism. Each of the test compounds was administered orally to the mice, one hour after the inoculation. The therapeutic effect of each compounds was judged by using a 50% effective dose ($ED_{50}$) from the survival rate on day 7 after injection by the Probit method as described in Proc. Soc. Exp. Biol. Med., Vol. 57, p.261-264, 1944. The Minimum inhibitory concentrations (MIC) were also measured. The results are shown in Table 2.

TABLE 2

| Organisms | Challenge dose (cells/mouse) | Test compound | MIC(μg/ml) | $ED_{50}$(mg/mouse)** |
|---|---|---|---|---|
| S. aureus Smith* | $2.13 \times 10^6$ [792 $LD_{50}$] | Compound A | 0.012 | 0.068(0.044-0.104) |
| | | OFLX | 0.20 | 0.380(0.253-0.601) |
| | | CPFX | 0.10 | 0.325(0.232-0.453) |
| S. aureus 109(MRSA)* | $4.93 \times 10^8$ [5.7 $LD_{50}$] | Compound A | 0.20 | 0.061(0.041-0.093) |
| | | OFLX | 0.78 | 0.459(0.257-0.661) |
| | | CPFX | 1.56 | 1.163(0.460-1.660) |
| S. pyogenes C-203 | $4.42 \times 10^4$ [680 $LD_{50}$] | Compound A | 0.05 | 0.214(0.124-0.388) |
| | | OFLX | 0.78 | 1.432(1.006-2.393) |
| | | CPFX | 0.39 | >2 |
| S. pneumoniae Type III | $6.0 \times 10^2$ [12 $LD_{50}$] | Compound A | 0.05 | 0.707(0.453-1.104) |
| | | OFLX | 1.56 | >2 |
| | | CPFX | 0.78 | >2 |
| E. coli KC-14* | $5.75 \times 10^4$ [488 $LD_{50}$] | Compound A | 0.05 | 0.028(0.019-0.042) |
| | | OFLX | 0.025 | 0.018(0.013-0.026) |
| | | CPFX | ≦0.006 | 0.011(0.008-0.015) |

(The overnight cultures of test organisms with an asterisk (*) were diluted with 50% mucin and 0.5 ml of each was injected intraperitoneally into mice. A double asterisk (**) means a 95% confidence limit. MRSA means methycillin-resistant Staphylococcus aureus.)

EXPERIMENT 3 : Acute toxicity

The compound A was intraveneously (iv) or orally (po) administered to a group of male mice once. After 10 days, the $LD_{50}$ values were determined by the Litchfield-Wilcoxon method. The result are shown in Table 3.

TABLE 3

| Route | $LD_{50}$ (mg/kg) |
|---|---|
| iv | 210 (185-230) |
| po | >3000 |

As shown in Table 1 and Table 2, the compounds of the present invention exhibit superior antibacterial activities against gram-positive bacteria than ofloxacin and ciprofloxacin. These enhanced in vitro antibacterial activities of the compounds of the present invention against gram-positive bacteria were well reflected in their protective effects against experimental infection in mice.

According to the various pharmacological experiments including the above-mentioned experiments, the compounds of formula (I) of the present invention and the corresponding salts, hydrates, alkyl esters, aralkyl esters and esters which are readily hydrolyzable in vivo, possess enhanced and broad antibacterial activities in vitro ad in vivo against gram-positive bacteria in comparison with the conventional pyridonecarboxylic acid, have better absorption by oral administration to experimental animals, show less serious side effects and low toxicity, and are expected to bear a clinical utility.

The compounds of the present invention, when used for the purpose of the treatment of various infectious diseases caused by the pathogenic microorganisms such as Staphylococcus aureus, S. epidermidis, Streptococcus pyogenes, S. viridans, S. pneunoniae, S. sarivaris, S. lactis, Enterococcus faecalis, Corynebacterium diphtheriae, Bacillus subtilis, Aerococcus viridans, Pediococcus damnosus, Micrococcus luteus, Escherichia coli, Shigella typhosa, S. flexneri, S. sonnei, Klebsiella pneumoniae, Proteus vulgaris, Morganella morganii, Proteus mirabilis, Serratia marcescens, Acinetobacter calcoaceticus, Aerobacter aerogenes, Alcaligenes faecalis, Citrobacter freundii, Enterobacter cloacae, Flavobacterium meningosepticum, Pseudomonas aeruginosa, Ps. cepacia, Ps. putida or Xanthomonas maltophilia, can be administrated orally, parenterally or externally in the form of a conventional pharmaceutical composition by mixing a therapeutically effective amount of the compounds of the present invention with a pharmaceutically acceptable carrier such as organic or inorganic, and solid or liquid vehicles.

Such composition includes, for example, a solid preparation such as tables, granules, powder and capsules, and a liquid preparation such as a suspension, syrup, emulsion and lemonade.

Moreover, the composition mentioned above can include, if necessary, an adjuvant, a stabilizer, a humectant and other conventional additive agents such as lactose, magnesium stearate, kaolin, sucrose, corn starch, talc, stearic acid, gelatin, agar, pectin, peanut oil, olive oil, cacao butter, ethylene glycol, and so on.

The dosage may vary depending on the age and symptoms of patients in need of the treatment, the kind of disease and the kind of the administered compound, but preferably ranges the 1 to about 4,000 mg or more a day. The single mean doses of the compounds of the present invention are about 50 mg, 100 mg, 250 mg, 500 mg, 1000 mg or 2000 mg.

The present invention will be more concretely explained by the following working and reference examples, but they should not be thought to limit the scope of the invention.

REFERENCE EXAMPLE 1

A mixture of 22.5 g of 4-benzyl-2-chloromethylmorpholine, 200 ml of ethanol and 200 ml of an aqueouos 26,7% dimethylamine solution is heated at 150° C. for 5 hours in an autoclave. After completion of the reaction, the solvent is distilled off under reduced pressure. After adding water, the residue is extracted with toluene three times. The extract is washed with water and dried over anhydrous magnesium sulfate. The solvent is distilled off under reduced pressure and the residue is treated with 37% hydrochloric acid-ethanol to give 2-(N,N-dimethylaminomethyl)-4-benzylmorpholine dihydrochloride as white crystals. A mixture of 22.9 g of the hydrochloride compound, 200 ml of ethanol and 100 ml of water is subjected to catalytic reduction with 2.3 g of 10% palladium-carbon at ordinary temperature and atmospheric pressure. After absorbing a theoretical volume of the hydrogen, the catalyst is filtered off and the filtrate is concentrated under reduced pressure. The obtained residue is treated with ethanol to give 2-(N,N-dimethylaminomethyl)morpholine dihydrochloride as white crystals, melting at 270°–271° C.

REFERENCE EXAMPLE 2

A mixture of 58 g of 2-chloromethyl-4-benzylmorpholine, 62.3 g of N-benzyl-N-methylamine and 38.6 g of sodium iodide in 220 ml of dimethylformamide is refluxed under stirring at 140° C. for 6 hours. After completion of the reaction, the dimethylformamide is distilled off under reduced pressure, water is added to the residue and the mixture is subjected to extraction with ethyl acetate. After washing with water, the resultant mixture is dried over anhydrous magnesium sulfate and the solvent is distilled off under reduced pressure. The residue is treated in 37% hydrochloric acid-ethanol to give 2-(N-benzyl-N-methylaminomethyl)-4-benzylmorpholine dihydrochloride as white crystals. The obtained hydrochloride compound (29.7 g) is subjected to catalytic reduction with 50 ml of ethanol, 80 ml of water and 3 g of 10% palladium-carbon. After absorbing the theoretical volume of the hydrogen, the catalyst is filtered off and the solvent of the filtrate is distilled off to give 2-(methylaminomethyl)morpholine dihydrochloride monohydrate as white crystals, melting at 122°–124° C.

REFERENCE EXAMPLE 3

To a solution of 62 g of 2-(N-benzyl-N-methylaminomethyl)-4-benzylmorpholine in 300 ml of toluene is added 47.7 g of ethyl chlorocarbonate and then the system heated at 80° C. for an hour. After completion of the reaction, the toluene is distilled off under reduced pressure and then the residue is distilled off under reduced pressure to give 43 g of 2-(N-methyl-N-ethoxycarbonylaminomethyl)-4-ethoxycarbonylmorpholine, boiling at 145°–154° C./0.8–0.9 mmHg. To a solution of 37.8 g of the compound thus obtained in 300 ml of ethanol is added 46.4 g of potassium hydroxide and the system refluxed at 80° C. for 20 hours. After completion of the reaction, insoluble materials are filtered off and the filtrate is concentrated under reduced pressure. The residue is distilled under reduced pressure to give 2-(methylaminomethyl)morpholine, boiling at 77°–83° C./18 mmHg.

REFERENCE EXAMPLE 4

A mixture of 31.8 g of 2-chloromethyl-4-benzylmorpholine and 30.5 g of potassium phthalimide in 200 ml of dimethylformamide is refluxed for 4 hours and then poured into water. The precipitated crystals are collected by filtration and dried to give 40.2 g of 2-phthalimidomethyl-4-benzylmorpholine. To 400 ml of the ethanol solution of this product is added dropwise a solution of 12.3 g of hydrazine hydrate in 100 ml of ethanol. Further, the resultant mixture is refluxed for 30 minutes. After cooling, insoluble materials are filtered off and the filtrate is concentrated under reduced pressure to give 2-aminomethyl-4-benzylmorpholine as an oily substance. To the solution of 10.3 g of the obtained product in 400 ml of ethanol and 40 ml of water are added 11 g of concentrated hydrochloric acid and 1.1 g of 10% palladium-carbon and the mixture subjected to catalytic reduction at ordinary temperature and atmospheric pressure. After absorbing the theoretical volume of the hydrogen, the catalyst is filtered off and the filtrate is concentrated under reduced pressure. The obtained residue is treated with ethanol-acetone to give 2-(aminomethyl)morpholine dihydrochloride as white crystals, melting at 215°–218° C.

REFERENCE EXAMPLE 5

By the use of 2-chloromethyl-4-benzylmorpholine and N-benzyl-N-ethylamine, the reaction is similarly carried out as Reference example 2 to give 2-(ethylaminomethyl)morpholine dihydrochloride as white crystals, melting at 222°–223° C.

REFERENCE EXAMPLE 6

By the use of 2-chloromethyl-4-benzylmorpholine and piperidine, the reaction is similarly carried out as Reference example 2 to give 2-(piperidinomethyl)morpholine dihydrochloride as white crystals, melting at 172°–174° C. with decomposition.

REFERENCE EXAMPLE 7

By the use of 2-chloromethyl-4-benzylmorpholine and morpholine, the reaction is similarly carried out as Reference example 2 to give 2-(morpholinomethyl)-morpholine dihydrochloride as white crystals, melting at 297°–299° C. with decompostion.

REFERENCE EXAMPLE 8

By the use of 2-chloromethyl-4-benzylmorpholine and N-methylpiperazine, the reactin is similarly carried out as Reference example 2 to give 2-(4-methyl-1-piperazinylmethyl) morpholine.trihydrochloride as white crystals, melting at 210°–212° C.

REFERENCE EXAMPLE 9

By the use of 2-chloromethyl-4-benzylmorpholine and N-formylpiperazine, the reaction is similarly carried out as Reference example 2 to give 2-(4-formyl-1-piperazinylmethyl) morpholine.dihydrochloride as white crystals, melting at 243°–245° C. with decomposition.

REFERENCE EXAMPLE 10

A mixture of 8.55 g of 2-(2-chloroethyl)-4-benzylmorpholine and 9.5 g of N-benzyl-N-methylamine in 70 ml of dimethylformamide is refluxed for 16 hours. After completion of the reaction, the solvent is concentrated under reduced pressure, and to the concentrate is added water followed by extracting with ethyl acetate. After washing with water, the extract is dried over anhydrous magnesium sulfate.

The solvent is concentrated under reduced pressure and the residue is treated with 25% hydrochloric acid-ethanol in ethanol to give 2-[2-(N-benzyl-N-methylamino)ethyl]-4-benzylmorpholine dihydrochloride as white crystals, melting at 256°–258° C. with decomposition. The obtained hydrochloride compound (5.25 g) is subjected to catalytic reduction with 1 g of 10% palladium-carbon in 50 ml of water and 200 ml of ethanol. After absorbing the theoretical volume of the hydrogen, the catalyst is filtered off and the filtrate is concentrated under reduced pressure. The residue is treated with ethanol to give 2-(2-methylaminoethyl)-morpholine dihydrochloride, melting at 179°–181° C. with decomposition.

The starting compound, 2-(2-chloroethyl)-4-benzylmorpholine is novel and can be prepared by the following manner.

To 200 ml of toluene is added 58 g of a solution of 70% RDB in toluene and to the mixture is added dropwise a solution of 26.3 of ethyl 4-benzyl-2-morpholinylacetate in 50 ml of toluene below 10° C. Further, after ice-cooling for 30 minutes, the mixture is stirred at room temperature overnight. After to the reaction mixture is successively added 20 ml of acetone and 100 ml of water, the inorganic substance precipitated is filtered off. The toluene layer is separated from the filtrate and dried over anhydrous magnesium sulfate. The solvent is concentrated under reduced pressure and the residue is purified by chromatography on silica gel to give 10.1 g of 2-(4-benzyl-2-morpholinyl)ethanol. To a mixture of 2.21 g of 2-(4-benzyl-2-morpholinyl)ethanol in 30 ml of chloroform is added 2.30 g of thionyl chloride and the system refluxed for 2.5 hours. After completion of the reaction, the solvent is concentrated under reduced pressure and to the residue are added water and ether. After neutralizing with potassium carbonate, the ether layer is separated and dried over anhydrous magnesium sulfate. The solvent is concentrated under reduced pressure to give 2.90 g of 2-(2-chloroethyl)-4-benzylmorpholine as an oily substance.

REFERENCE EXAMPLE 11

37.7 g of 2-(p-toluenesulfonyloxymethyl)-4-benzylmorpholine, prepared by the method as described in Synthetic Communications, Vol. 10(1), p.59, 1980, 14.9 g of N-benzyl-N-ethylamine and 4.5 g of sodium iodide are refluxed with stirring in 200 ml f dimethylformamide at 140° C. for 8 hours. After completion of the reaction, the dimethylformamide is distilled off under reduced pressure, to the residue is added water and extracted with ethyl acetate. After washing with water, the extract is dried over anhydrous magnesium sulfate and the solvent is distilled off under reduced pressure. The residue is treated in 37% hydrochloric acid-ethanol to give 2-(N-benzyl-N-ethylaminomethyl)-4-benzylmorpholine dihydrochloride as white crystals. The obtained hydrochloride compound is subjected to debenzylation as Reference example 2 to give 2-(ethylaminomethyl)morpholine dihydrochloride as white crystals, melting at 222°–223° C.

REFERENCE EXAMPLE 12

By the use of 2-chloromethyl-4-benzylmorpholine and pyrrolidine, the reaction is similarly carried out as Reference example 2 to give 2-(1-pyrrolidinylmethyl)-morpholine.

REFERENCE EXAMPLE 13

By the use of 2-chloromethyl-4-benzylmorpholine and piperazine, the reaction is similarly carried out as Reference example 2 to give 2-(1-piperazinylmethyl)-morpholine.

REFERENCE EXAMPLE 14

(1) A suspension of 26.4 g of ethyl 2,3,4,5-tetrafluorobenzoylacetate, 18.7 g of 2-(dimethylaminomethyl)morpholine and 8.4 g sodium hydrogencarbonate in 130 ml of acetonitrile is refluxed for 7 hours. The reaction mixture is concentrated under reduced pressure, to the obtained residue is added 100 ml of chloroform and the solution is washed with water. After drying over anhydrous magnesium sulfate, the chloroform is distilled off under reduced pressure and the residue is purified by chromatography on silica gel to give 29.9 g of ethyl 4-[2-(dimethylaminomethyl)morpholino]-2,3,5-trifluorobenzoylacetate in 77% yield as an oily substance.

NMR (CDCl$_3$), δ (ppm): 1.27 (3H, t, J=7Hz), 2.28 (6H, s),
4.21 (2H, q, J=7Hz), 7.26–7.52 (1H, m)

(2) A solution of 3.88 g of ethyl 4-[2-(dimethylaminomethyl)-morpholino]-2,3,5-trifluorobenzoylacetate and 1.85 g of dimethylformamide dimethylacetal in 20 ml of toluene is refluxed for 6 hours. The reaction mixture is concentrated under reduced pressure and to the obtained residue is added 20 ml of ethanol. After the addition of 0.94 g of cyclopropylamine under ice-cooling, the mixture is stirred at room temperature for 3 hours. The reaction mixture is concentrated under reduced pressure and the obtained residue is purified by chromatography on silica gel to give 4.06 g of ethyl 2-[4-[2-(dimethylaminomethyl)morpholino]-2,3,5-trifluorobenzoyl]-3-cyclopropylaminoacrylate in 89% yield as an oily substance.

NMR (CDCl$_3$), δ (ppm): 0.72–1.02 (4H, m),
1.13 (3H, t, J=7Hz), 2.28 (6H, s),
4.08 (2H, q, J=7Hz), 6.70–6.92 (1H, m),
8.14 (1H, d, J=14Hz)

REFERENCE EXAMPLE 15

(1) A suspension of 26.4 g of ethyl 2,3,4,5-tetrafluorobenzoylacetate, 18.7 g of 2-(N-ethoxycarbonyl-N-methylaminomethyl)morpholine and 8.4 g of sodium hydrogen carbonate in 130 ml of acetonitrile is refluxed for 7 hours. The reaction mixture is concentrated under reduced pressure, to the obtained residue is added 100 ml of chloroform and the solution is washed with water. After drying over anhydrous magnesium sulfate, the chloroform is distilled off under reduced pressure and the residue is purified by chromatography on silica gel to give 30.0 g of ethyl 4-[2-(N-ethoxycarbonyl-N-methylaminomethyl)morpholino]-2,3,5-trifluorobenzoylacetate in 67% yield, as an oily substance.

NMR (CDCl$_3$), δ (ppm): 1.27 (3H, t, J=7Hz),
1.28 (3H, t, J=7Hz), 3.00 (3H, s),
4.14 (2H, q, J=7Hz), 7.08–7.52 (1H, m) (2) A solution of 4.46 g of ethyl 4-[2-(N-ethoxycarbonyl-N-methylaminomethyl)morpholino]-2,3,5-trifluorobenzoylacetate, 1.85 g of dimethylformamide dimethylacetal and 20 ml of toluene is refluxed for 6 hours. The reaction mixture is concentrated under reduced pressure and to the obtained residue is added 20 ml of ethanol. After the addition of 0.94 g of cyclopropylamine with ice-cooling, the mixture is stirred at room temperature for 3 hours. The reaction mixture is concentrated under reduced pressure and the obtained residue is purified by chromatography on silica gel to give 4.06 g of ethyl 2-[4-[2-(N-ethoxycarbonyl-N-methylaminomethyl)morpholino]-2,3,5-trifluorobenzoyl]-3-cyclopropylaminoacrylate in 89% yield, as an oily substance.

NMR (CDCl$_3$), δ (ppm): 0.78–0.95 (4H, m),
0.96 and 1.10 (3H, t, J=7Hz),
1.27 (3H, t, J=7Hz), 3.00 (3H, s),
.4.02 and 4.07 (2H, q, J=7Hz),
4.13 (2H, q, J=7Hz),
6.82–6.88 and 6.97–7.03 (1H, m),
8.12 and 8.17 (1H, d, J=14Hz),
9.34–9.44 and 10.75–10.86 (1H, br)

REFERENCE EXAMPLE 16

(1) A suspension of 22.2 g of ethyl 2,3,4,5-tetrafluorobenzoate, 22.2 g of 2-(N-ethoxycarbonyl-N-methylaminomethyl)morpholine and 8.4 g of sodium hydrogen carbonate in 130 ml of acetonitrile is refluxed for 7 hours. The reaction mixture is concentrated under reduced pressure, to the obtained residue is added 100 ml of chloroform and the solution is washed with water. After drying over anhydrous magnesium sulfate, the chloroform is distilled off under reduced pressure and the residue is puiified by chromatography on silica gel to give 29.0 g of ethyl 4-[2-(N-ethoxycarbonyl-N-methylaminomethyl)morpholino]-2,3,5-trifluorobenzoate in 72% yield, as an oily substance.

NMR (CDCl$_3$), δ (ppm): 1.25 (3H, t, J=7Hz),
1.38 (3H, t, J=7Hz), 3.00 (3H, s),
4.13 (2H, q, J=7Hz), 4.36 (2H, q, J=7Hz),
7.20–7.49 (1H, m)

(2) To a solution of 19.1 g of ethyl 4-[2-(N-ethoxycarbonyl-N-methylaminomethyl)morpholino]-2,3,5-trifluorobenzoate in 100 ml of methanol is added dropwise a solution of 7.56 g of sodium hydroxide in 100 ml of water under ice-cooling. After stirring under ice-cooling for 20 minutes, the methanol is distilled off under reduced pressure. The solution is washed with ethyl acetate, made acid with 6 N hydrochloric acid and then extracted with ethyl acetate. After drying over anhydrous magnesium sulfate, the ethyl acetate is distilled off under reduced pressure. To the residue is added isopropyl ether. The obtained crystals are filtered with suction and dried to give 12.2 g of 4-[2-(N-ethoxycarbonyl-N-methylaminomethyl)-morpholino]-2,3,5-trifluorobenzoic acid in 68% yield, melting at 170°–172° C.

NMR (DMSO d$_6$), δ (ppm): 1.18 (3H, t, J=7Hz),
2.88 (3H, s), 4.02 (2H, q, J=7Hz), 7.28–7.52 (1H, m)

(3) A solution of 6.1 g of 4-[2-(N-ethoxycarbonyl-N-methylaminomethyl) morpholino]-2,3,5-trifluorobenoic acid, 4.82 g of thionyl chloride and a catalytic amount of dimethylformamide is refluxed for 4 hours. The reaction mixture is concentrated under reduced pressure to give 4-[2-(N-ethoxycarbonyl-N-methylaminomethyl)-morpholino]-2,3,5-trifluorobenzoic acid chloride. The acid chloride compound without purification is used in the following step. (4) A suspension of 0.79 g of magnesium in the form of thin turnings in 2 ml of ethanol and 10 ml of toluene is heated at 75° C. and the reaction is initiated with adding a few drops of tetrachloromethane. To the reaction mixture is added dropwise a solution of 5.19 g of diethyl malonate, 3 ml of ethanol and 20 ml of toluene at the same temperature for 20 minutes and further stirred for 2 hours. After cooling the reaction mixture to a temperature below 0° C., to the reaction mixture is added dropwise 1 ml of dimethylformamide. To the reaction mixture is added dropwise a solution of 4-[2-(N-ethoxycarbonyl-N-methylaminomethyl)morpholino]-2,3,5-trifluorobenzoic acid chloride in 4 ml of toluene. After stirring for 2 hours, to the reaction mixture is added dropwise 16 ml of 5% hydrochloric acid under ice-cooling and the system stirred for 30 minutes. The organic layer is separated and the aqueous layer is extracted with 20 ml of toluene. The organic layer combined is washed with water, dried over anhydrous magnesium sulfate and then concentrated under reduced pressure. To the obtained residue are added 20 mg of p-toluenesulfonic acid and 20 ml of water and the system refluxed for 16 hours. After the resultant mixture is extracted with chloroform and the extract is washed with water it is dried over anhydrous magnesium sulfate and then concentrated under reduced pressure to give ethyl 4-[2-(N-ethoxycarbonyl-N-methylaminomethyl)morpholino]-2,3,5-trifluorobenzoylacetate as an oily substance. The NMR values of this compound are identical with those of the compound obtained by Reference example 15(1).

REFERENCE EXAMPLE 17

A suspension of 3.36 g of diethyl 2,3,4,5-tetrafluorobenzoylmalonate, 2.22 g of 2-(N-ethoxycarbonyl-N-methylaminomethyl)morpholine and 0.84 g of sodium hydrogen carbonate in 13 ml of acetonitrile is refluxed for 5 hours., The reaction mixture is concentrated under reduced pressure, to the obtained residue is added 20 ml of chloroform and it is washed with water. After drying over anhydrous magnesium sulfate, the chloroform is distilled off under reduced pressure and to the residue are added 20 mg of p-toluenesulfonic acid and 20 ml of water. After refluxing for 16 hours, the resultant mixture is extracted with chloroform. The extract is washed with water, dried over anhydrous magnesium sulfate and concentrated under reduced pressure to give ethyl 4-[2-(N-ethoxycarbonyl-N-methylaminomethyl)morpholino]-2,3,5-trifluorobenzoylacetate as an oily substance. The NMR values of this compound are identical with those of the compound obtained by Reference example 15(1).

EXAMPLE 1

A solution of 813 mg of 1-ethyl-6,7,8-trifluoro-1,4-dihydro-4-oxoquinoline-3-carboxylic acid, 650 mg of 2-(formylaminomethyl)morpholine hydrochloride and 1.0 g of 1,8-diazabicyclo[5.4.0]undec-7-ene in 10 ml of acetonitrile is refluxed for 3 hours and allowed to stand at room temperature overnight. The precipitated crystals are collected by filtration and successively washed with acetonitrile, water and acetone to give 1-ethyl-6,8-difluoro-7-[2-(formylaminomethyl)morpholino]-1,4-dihydro-4-oxoquinoline-3-carboxylic acid, melting at 234°–236° C.

EXAMPLE 2

A solution of 500 mg of 1-ethyl-6,8-difluoro-7-[2-(formylaminomethyl)morpholino]-1,4-dihydro-4-oxoquinoline-3-carboxylic acid, 1 ml of concentrated hydrochloric acid, 2 ml of water and 10 ml of methanol is refluxed for 1.5 hours. The reaction mixture is concentrated under reduced pressure. The obtained crystals are washed with acetone, collected by filtration and recrystallized from dimethylformamide to give 7-[2-(aminomethyl)morpholino]-1-ethyl-6,8-difluoro-1,4-dihydro-4-oxoquinoline-3-carboxylic acid hydrochloride, melting at 276°–278° C. with decomposition.

EXAMPLE 3

By the use of 1-ethyl-6,7,8-trifluoro-1,4-dihydro-4-oxoquinoline-3-carboxylic acid and 2-(methylaminomethyl)morpholine, the reaction is similarly carried out as Example 1 to give 1-ethyl-6,8-difluoro-1,4-dihydro-7-[2-(methylaminomethyl)morpholino]-4-oxoquinoline-3-carboxylic acid, melting at 229°–231° C. (when recrystallized from dimethylformamide).

EXAMPLE 4

By the use of 1-ethyl-6,7,8-trifluoro-1,4-dihydro-4-oxoquinoline-3-carboxylic acid and 2-(ethylaminomethyl)morpholine, the reaction is similarly carried out as Example 1 to give 1-ethyl-7-[2-(ethylaminomethyl)morpholino]-6,8-difluoro-1,4-dihydro-4-oxoquinoline-3-carboxylic acid, melting at 183°–186° C. (when recrystallized from dimethylformamide).

EXAMPLE 5

By the use of 1-ethyl-6,7,8-trifluoro-1,4-dihydro-4-oxoquinoline-3-carboxylic acid and 6-methyl-2-(methylaminomethyl)morpholine, the reaction is similarly carried out as Example 1 to give 1-ethyl-6,8-difluoro-1,4-dihydro-7-[6-methyl-2-(methylaminomethyl)morpholino]-4-oxoquinoline-3-carboxylic acid.

EXAMPLE 6

By the use of 1-ethyl-6,7,8-trifluoro-1,4-dihydro-4-oxoquinoline-3-carboxylic acid and 2-(dimethylaminomethyl)morpholine, the reaction is similarly carried out as Example 1 to give 1-ethyl-6,8-difluoro-1,4-dihydro-7-[2-(dimethylaminomethyl)morpholino]-4-oxoquinoline-3-carboxylic acid, melting at 185°–188° C. (when recrystallized from acetonitrile).

EXAMPLE 7

By the use of 1-ethyl-6,7,8-trifluoro-1,4-dihydro-4-oxoquinoline-3-carboxylic acid and 2-(2-formylaminoethyl)morpholine, the reaction is similarly carried out as Example 1 to give 1-ethyl-6,8-difluoro-7-[2-(2-formylaminoethyl)morpholino]-1,4-dihydro-4-oxoquinoline-3-carboxylic acid.

EXAMPLE 8

By the use of 1-ethyl-6,8-difluoro-7-[2-(2-formylaminoethyl)morpholino]-1,4-dihydro-4-oxoquinoline-3-carboxylic acid, the reaction is similarly carried out as Example 2 to give 7-[2-(2-aminoethyl)morpholino]-1-ethyl-6,8-difluoro-1,4-dihydro-4-oxoquinoline-3-carboxylic acid.

EXAMPLE 9

By the use of 1-ethyl-6,7,8-trifluoro-1,4-dihydro-4-oxoquinoline-3-carboxylic acid and 2-(2-methylaminoethyl)morpholine, the reaction is similarly carried out as Example 1 to give 1-ethyl-6,8-difluoro-1,4-dihydro-7-[2-(2-methylaminoethyl)morpholino]-4-oxoquinoline-3-carboxylic acid.

EXAMPLE 10

By the use of 1-ethyl-6,7,8-trifluoro-1,4-dihydro-4-oxoquinoline-3-carboxylic acid and 2-(2-ethylaminoethyl)morpholine, the reaction is similarly carried out as Example 1 to give 1-ethyl-7-[2-(2-ethylaminoethyl)morpholino]-6,8-difluoro-1,4-dihydro-4-oxoquinoline-3-carboxylic acid.

EXAMPLE 11

A solution of 8.3 g of 1-cyclopropyl-6,7,8-trifluoro-1,4-dihydro-4-oxoquinoline-3-carboxylic acid, 7.1 g of 2-(methylaminomethyl)morpholine dihydrochloride and 15.2 g of 1,8-diazabicyclo[5.4.0]undec-7-ene in 166 ml of acetonitrile is refluxed for 8 hours. After ice-cooling, the precipitated crystals are collected by filtration, washed with acetone and recrystallized from dimethylformamide to give 1-cyclopropyl-6,8-difluoro-1,4-dihydro-7-[2-(methylaminomethyl)-morpholino]-4-oxoquinoline-3-carboxylic acid, melting at 257°–259° C. with decomposition. The corresponding hydrochloride melts at 288°–290° C. with decomposition.

EXAMPLE 12

By the use of 1-cyclopropyl-6,7,8-trifluoro-1,4-dihydro-4-oxoquinoline-3-carboxylic acid and 2-(ethylaminomethyl)morpholine, the reaction is similarly carried out as Example 11 to give 1-cyclopropyl-7-[2-(ethylaminomethyl)morpholino]6,8-difluoro-1,4-dihydro-4-oxoquinoline-3-carboxylic acid, melting at 210°–213° C. with decomposition.

EXAMPLE 13

By the use of 1-cyclopropyl-6,7,8-trifluoro-1,4-dihydro-4-oxoquinoline-3-carboxylic acid and 2-(formylaminomethyl)morpholine, the reaction is similarly carried out as Example 11 to give 1-cyclopropyl-6,8-difluoro-7-[2-(formylaminomethyl)morpholino]-1,4-dihydro-4-oxoquinoline-3-carboxylic acid, melting at 210°–213° C.

EXAMPLE 14

By the use of 1-cyclopropyl-6,8difluoro-7-[2-(formylaminomethyl)morpholino]-1,4-dihydro-4-oxoquinoline-3-carboxylic acid, the reaction is similarly carried out as Example 2 to give 7-[2-(aminomethyl)morpholino]-1-cyclopropyl-6,8-difluoro-1,4-dihydro-4-oxoquinoline-3-carboxylic acid hydrochloride, melting at 277°–279° C. with decomposition.

EXAMPLE 15

By the use of 1-cyclopropyl-6,7,8-trifluoro-1,4-dihydro-4-oxoquinoline-3-carboxylic acid and 2-(dimethylaminomethyl)morpholine, the reaction is similarly carried out as Example 1 to give 1-cyclopropyl-7-[2-(dimethylaminomethyl)morpholino]-6,8-difluoro-1,4-dihydro-4-oxoquinoline-3-carboxylic acid, melting at 182°–183° C.

EXAMPLE 16

By the use of 1-cyclopropyl-6,7,8-trifluoro-1,4-dihydro-4-oxoquinoline-3-carboxylic acid and 2-(diethylaminomethyl)morpholine, the reaction is similarly carried out as Example 11 to give 1-cyclopropyl-7-[2-(diethylaminomethyl)morpholino]-6,8-difluoro-1,4-dihydro-4-oxoquinoline-3-carboxylic acid, melting at 155°–157° C.

EXAMPLE 17

By the use of 1-cyclopropyl-6,7,8-trifluoro-1,4-dihydro-4-oxoquinoline-3-carboxylic acid and 2-(1-pyrrolidinylmethyl)morpholine, the reaction is similarly carried out as Example 11 to give 1-cyclopropyl-6,8-difluoro-1,4-dihydro-4-oxo-7-[2-(1-pyrrolidinylmethyl)morpholino]quinoline-3-carboxylic acid.

EXAMPLE 18

By the use of 1-cyclopropyl-6,7,8-trifluoro-1,4-dihydro -4-oxoquinoline-3-carboxylic acid and 2-(piperidinomethyl)morpholine, the reaction is similarly carried out as Example 11 to give 1-cyclopropyl-6,8-difluoro-1,4-dihydro-4-oxo-7-[2-(piperidinomethyl)morpholino]quinoline-3-carboxylic acid 1/2 hydrate, melting at 160°–162° C.

EXAMPLE 19

By the use of 1-cyclopropyl-6,7,8-trifluoro-1,4-dihydro-4-oxoquinoline-3-carboxylic acid and 2-(morpholinomethyl)morpholine, the reaction is similarly carried out as Example 11 to give 1-cyclopropyl-6,8-difluoro-1,4-dihydro-7-[2-(morpholinomethyl)morpholino]-4-oxoquinoline-3-carboxylic acid, melting at 171°–172° C.

EXAMPLE 20

By the use of 1-cyclopropyl-6,7,8-trifluoro-1,4-dihydro-4-oxoquinoline-3-carboxylic acid and 2-(1-piperazinylmethyl)morpholine, the reaction is similarly carried out as Example 11 to give 1-cyclopropyl-6,8-difluoro-1,4-dihydro-4-oxo-7-[2-(1-piperazinylmethyl)morpholino]quinoline-3-carboxylic acid. dihydrochloride.1/2 hydrate, melting at 260° C. with decomposition.

EXAMPLE 21

By the use of 1-cyclopropyl-6,7,8-trifluoro-1,4-dihydro-4-oxoquinoline-3-carboxylic acid and 2-(N-methyl-1-piperazinylmethyl)morpholine, the reaction is similarly carried out as Example 11 to give 1-cyclopropyl-6,8-difluoro-1,4-dihydro-7-[2-(N-methyl-1-piperazinylmethyl)morpholino]-4-oxoquinoline-3-carboxylic acid.

EXAMPLE 22

By the use of 1-cyclopropyl-6,7,8-trifluoro-1,4-dihydro-4-oxoquinoline-3-carboxylic acid and 2-(2-formylaminoethyl)morpholine, the reaction is similarly carried out as Example 11 to give 1-cyclopropyl-6,8-difluoro-7-[2-(2-formylaminoethyl)morpholino]-1,4-dihydro-4-oxoquinoline-3-carboxylic acid.

EXAMPLE 23

By the use of 1-cyclopropyl-6,8-difluoro-7-[2-(2-formylaminoethyl)morpholino]-1,4-dihydro-4-oxoquinoline-3-carboxylic acid, the reaction is similarly carried out as Example 2 to give 7-[2-(2-aminoethyl)morpholino]-1-cyclo- propyl-6,8-difluoro-1,4-dihydro-4-oxoquinoline-3-carboxylic acid.

EXAMPLE 24

By the use of 1-cyclopropyl-6,7,8-trifluoro-1,4-dihydro-4-oxoquinoline-3-carboxylic acid and 2-(2-methylaminoethyl)morpholine, the reaction is similarly carried out as Example 11 to give 1-cyclopropyl-6,8-difluoro-1,4-dihydro-7-[2-(2-methylaminoethyl)morpholino]-4-oxoquinoline-3-carboxylic acid 1/4 hydrate, melting at 243°–251° C. with decomposition.

EXAMPLE 25

By the use of 1-cyclopropyl-6,7,8-trifluoro-1,4-dihydro-4-oxoquinoline-3-carboxylic acid and 2-(2-ethylaminoethyl)morpholine, the reaction is similarly carried out as Example 11 to give 1-cyclopropyl-7-[2-(2-ethylaminoethyl)morpholino] -1,4-dihydro-4-oxoquinoline-3-carboxylic acid.

EXAMPLE 26

A solution of 710 mg of 1-(2,4-difluorophenyl)-6,7,8-trifluoro-1,4-dihydro-4-oxoquinoline-3-carboxylic acid, 487 mg of 2-(methylaminomethyl)morpholine dihydrochloride and 1035 mg of 1,8-diazabicyclo[5.4.0]undec-7-ene in 10 ml of acetonitrile is refluxed for 21 hours. The reaction mixture is concentrated under reduced pressure and to the residue is added 10 ml of methanol. The obtained crystals are collected by filtration and washed with methanol, water and then acetone to give 1-(2,4-difluorophenyl)-7-[2-(methylaminomethyl)morpholino]-6,8-difluoro-1,4-dihydro-4-oxoquinoline-3-carboxylic acid, melting at 224°–227° C. with decomposition.

EXAMPLE 27

By the use of 1-(2,4-difluorophenyl)-6,7,8-trifluoro-1,4-dihydro-4-oxoquinoline-3-carboxylic acid and 2-(ethylaminomethyl)morpholine, the reaction is similarly carried out as Example 26 to give 7-[2-(ethylaminomethyl)morpholino]-1(2,4-difluorophenyl)-6,8-difluoro-1,4-dihydro-4-oxoquinoline-3-carboxylic acid, melting at 226°–229° C. with decomposition. Examle 28

By the use of 1-(2,4-difluorophenyl)-6,7,8-trifluoro-1,4-dihydro-4-oxoquinoline-3-carboxylic acid and 2-(formylaminomethyl)morpholine, the reaction is similarly carried out as Example 26 to give 1-(2,4-difluorophenyl)-6,8-difluoro-7-[2-(formylaminomethyl)morpholino]-1,4-dihydro-4-oxoquinoline- 3-carboxylic acid, melting at 230°–233° C. with decomposition.

EXAMPLE 29

By the use of 1-(2,4-difluorophenyl)-6,8-difluoro-7-[2-(formylaminomethyl)morpholino]-1,4-dihydro-4-oxoquinoline-3-carboxylic acid, the reaction is similarly carried out as Example 2 to give 7-[2-(aminomethyl)-morpholino]-1-(2,4-difluorophenyl)-6,8-difluoro-1,4-dihydro-4-oxoquinoline-3-carboxylic acid hydrochloride, melting at 244°–246° C. with decomposition.

EXAMPLE 30

By the use of 1-(2,4-difluorophenyl)-6,7,8-trifluoro-1,4-dihydro-4-oxoquinoline-3-carboxylic acid and 2-(2formylaminoethyl)morpholine, the reaction is similarly carried out as Example 26 to give 1-(2,4-difluorophenyl)-6,8-difluoro-7-[2-(2-formylaminoethyl)morpholino]-1,4-dihydro-4-oxoquinoline-3-carboxylic acid.

EXAMPLE 31

By the use of 1-(2,4-difluorophenyl)-6,8-difluoro-7-[2-(2-formylaminoethyl)morpholino]-1,4-dihydro-4-oxoquinoline-3-carboxylic acid, the reaction is similarly carried out as Example 2 to give 7-[2-(2-aminoethyl)-morpholino]-1-(2,4-difluorophenyl)-6,8-difluoro-1,4-dihydro-4-oxoquinoline-3-carboxylic acid.

EXAMPLE 32

By the use of 1-(2,4-difluorophenyl)-6,7,8-trifluoro-1,4-dihydro-4-oxoquinoline-3-carboxylic acid and 2-(2-methylaminoethyl)morpholine, the reaction is similarly carried but as Example 26 to give 1-(2,4-difluorophenyl)-6,8-difluoro-1,4-dihydro-7-[2-(2-methylaminoethyl)morpholino]-4-oxoquinoline-3-carboxylic acid.

EXAMPLE 33

By the use of 1-(2,4-difluorophenyl)-6,7,8-trifluoro-1,4-dihydro-4-oxoquinoline-3-carboxylic acid and 2-(2ethylaminoethyl)morpholine, the reaction is similarly carried out as Example 26 to give 1-(2,4-difluorophenyl)-7-[2-(2ethylaminoethyl)morpholino]-6,8-difluoro-1,4-dihydro-4-oxoquinoline-3-carboxylic acid.

EXAMPLE 34

A mixture of a solution of 6.75 g of 2-chloromethyl-4-benzylmorpholine in 150 ml of ethanol with 0.5 g of 10% palladium-carbon is subjected to catalytic reduction at atmospheric pressure. After absorbing the theoretical volume of the hydrogen, the catalyst is filtered off. The filtrate is concentrated under reduced pressure to give 2-chloromethylmorpholine as an oily substance.

A solution of 0.54 g of 1-ethyl-6,7,8-trifluoro-1,4-dihydro-4-oxoquinoline-3-carboxylic acid and 0.60 g of 2-chloromethylmorpholine in 20 ml of dimethyl sulfoxide is stirred at 120° C. for 8 hours. The reaction mixture is concentrated under reduced pressure and to the residue is added water followed by extracting with chloroform. The organic layer is washed with water, dried over anhydrous magnesium sulfate and then the solvent is distilled off. Further, the obtained crystals are recrystallized from chloroform-methanol to give 7-(2-chloromethylmorpholino)-1-ethyl-6,8-difluoro-1,4-dihydro-4-oxoquinoline-3-carboxylic acid, melting at 212°–215° C.

A mixture of 397 mg of 7-(2-chloromethylmorpholino)-1-ethyl-6,8-difluoro-1,4-dihydro-4-oxoquinoline-3-carboxylic acid, 156 mg of pyrrolidine, 150 mg of sodium iodide and 15 ml of dimethylformamide is stirred at 150° C. for 7 hours. The reaction mixture is concentrated under reduced pressure and to the residue is added water followed by extracting with chloroform. The organic layer is washed with water, dried over anhydrous magnesium sulfate and then the solvent is distilled off to give 1-ethyl-6,8-difluoro-1,4-dihydro-4-oxo-7-[2-(1-pyrrolidinylmethyl)morpholino]quinoline-3-carboxylic acid.

EXAMPLE 35

By the use of 7-(2-chloromethylmorpholino)-1-ethyl-6,8-difluoro-1,4-dihydro-4-oxoquinoline-3-carboxylic acid and dimethylamine, the reaction is similarly carried out as Example 34 to give 7-[2-(dimethylaminomethyl)-morpholino]-1-ethyl-6,8-difluoro-1,4-dihydro-4-oxoquinoline-3-carboxylic acid, melting at 185°–188° C.

EXAMPLE 36

By the use of 7-(2-chloromethylmorpholino)-1-ethyl-6,8-difluoro-1,4-dihydro-4-oxoquinoline-3-carboxylic acid and diethylamine, the reaction is similarly carried out as Example 4 to give 7-[2-(diethylaminomethyl)-morpholino]-1-ethyl-6,8-difluoro-1,4-dihydro-4-oxoquinoline-3-carboxylic acid.

EXAMPLE 37

By the use of 7-(2-chloromethylmorpholino)-1-ethyl-6,8-difluoro-1,4-dihydro-4-oxoquinoline-3-carboxylic acid and piperidine, the reaction is similarly carried out as Example 34 to give 1-ethyl-6,8-difluoro-1,4-dihydro-4-oxo-7-[2-(piperidinomethyl)morpholino]quinoline-3-carboxylic acid.

EXAMPLE 38

By the use of 7-(2-chloromethylmorpholino)-1-ethyl-6,8-difluoro-1,4-dihydro-4-oxoquinoline-3-carboxylic acid and morpholine, the reaction is similarly carried out as Example 34 to give 1-ethyl-6,8-difluoro-1,4-dihydro-7-[2-(morpholinomethyl)morpholind]-4-oxoquinoline-3-carboxylic acid.

EXAMPLE 39

By the use of 7-(2-chloromethylmorpholino)-1-ethyl-6,8-difluoro-1,4-dihydro-4-oxoquinoline-3-carboxylic acid and piperazine, the reaction is similarly carried out as Example 34 to give 1-ethyl-6,8-difluoro-1,4-dihydro-4-oxo-7-[7-(1-piperazinylmethyl)morpholino]quinoline-3-carboxylic acid.

EXAMPLE 40

By the use of 7-(2-chloromethylmorpholino)-1-ethyl-6,8-difluoro-1,4-dihydro-4-oxoquinoline-3-carboxylic acid and N-methylpiperazine, the reaction is similarly carried out as Example 34 to give 1-ethyl-6,8-difluoro-1,4-dihydro-7-[2-(N -methyl-1-piperazinylmethyl)morpholino]-4-oxoquinoline-3-carboxylic acid.

EXAMPLE 41

By the use of 1-ethyl-6,7,8-trifluoro-1,4-dihydro-4-oxoquinoline-3-carboxylic acid and 3-(aminomethyl)-morpholine, the reaction is similarly carried out as Example 1 to give 7-[3-(aminomethyl)morpholino]-1-ethyl-6,8-difluoro-1,4-dihydro-4-oxoquinoline-3-carboxylic acid.

EXAMPLE 42

By the use of 1-ethyl-6,7,8-trifluoro-1,4-dihydro-4-oxoquinoline-3-carboxylic acid and 3-(methylaminomethyl)morpholine, the reaction is similarly carried out as Example 1 to give 1-ethyl-6,8-difluoro-1,4-dihydro-7-[3-(methylaminomethyl)morpholino]-4-oxoquinoline-3-carboxylic acid.

EXAMPLE 43

2-Dimethylcarbamoylmethyl.1-ethyl-6,8-difluoro-1,4-dihydro-7-[2-(methylaminomethyl)morpholino]-4-oxoquinoline-3-carboxylate is obtained by reacting 1-ethyl-6,8-difluoro-1,4-dihydro-7-[2-(methylaminomethyl)morpholino]-4-oxoquinoline-3-carboxylic acid with N,N-dimethylchloroacetamide.

EXAMPLE 44

Pivaloyloxymethyl.1-ethyl-6,8-difluoro-1,4-dihydro-7-[2-(methylaminomethyl)morpholino]-4-oxoquinoline-3-carboxylate is obtained by reacting 1-ethyl-6,8-difluoro-1,4-dihydro-7-[2-(methylaminomethyl)morpholino]-4-oxoquinoline-3-carboxylic acid with chloromethyl pivalate.

EXAMPLE 45

5-Methyl-1,3-dioxolen-2-on-4-ylmethyl 1-cyclopropyl-6,8-difluoro-1,4-dihydro-7-[2-(methylaminomethyl)morpholino]-4-oxoquinoline-3-carboxylate is obtained by reacting 1-cyclopropyl6,8-difluoro-1,4-dihydro-7-[2-(methylaminomethyl)morpholino]-oxoquinoline-3-carboxylic acid with 4-bromomethyl-5-methyl1,3-dioxolen-2-on.

EXAMPLE 46

1-Ethoxycarbonyloxyethyl 1-cyclopropyl-6,8-difluoro-1,4-dihydro-7-[2-(methylaminomethyl)morpholino]-4-oxoquinoline-3carboxylate is obtained by reacting 1-cyclopropyl-6,8-difluoro-1,4-dihydro-7-[2-(methylaminomethyl)morpholino]-4-oxoquinoline-3-carboxylic acid with 1-chloroethyl ethyl carbonate.

EXAMPLE 47

By the use of 1-cyclopropyl-6,7,8-trifluoro-1,4-dihydro-4-oxoquinoline-3-carboxylic acid and 2-(N-benzyl-N-methylaminomethyl)morpholine, the reaction is similarly carried out as Example 11 to give 1-cyclopropyl-7-[2-(N-benzyl-N-methylaminomethyl)morpholino]-6,8-difluoro-1,4-dihydro-4-oxoquinoline-3-carboxylic acid, melting at 155°–157° C.

EXAMPLE 48

(1) A suspension of 4.0 g of ethyl 2-[4-[2-(dimethylaminomethyl)morpholino]-2,3,5-trifluorobenzoyl]-3-cyclopropylaminoacrylate obtained by Reference example 14(2) and 1.22 g of potassium carbonate in 20 ml of dimethylformamide is stirred under heating at 55°–60° C. for 8 hours. The reaction mixture is poured into 50 ml of ice-cold water.

The obtained precipitate is filtered with suction, rinsed with water well, dried and recrystallized from ethyl acetate to give 2.29 g of ethyl 1-cyclopropyl-6,8-difluoro-7-[2-(dimethylaminomethyl)morpholino]-1,4-dihydro-4-oxoquinoline-3-carboxylate in 60% yield, melting at 168°–169° C.

NMR (CDCl$_3$), δ (ppm): 1.04–1.32 (4H,m), 1.40 (3H, t, J=7Hz), 2.29 (6H, s), 4.38 (2H, q, J=7Hz), 7.90 (1H, dd, J=13.2Hz), 8.52 (1H, s)

(2) A solution of 2.21 g of ethyl 1-cyclopropyl-6,8-difluoro-7-[2-(dimethylaminomethyl)morpholino]-1,4-dihydro-4-oxoquinoline-3-carboxylate and 5 ml of concentrated hydrochloric acid in 10 ml of water and 10 ml of ethanol is refluxed, for 2.5 hours. The resultant mixture is concentrated under reduced pressure and to the obtained crystals is added ethanol. The crystals are filtered off with suction, washed with ethanol and then dried to give 1.82 g of 1-cyclopropyl-6,8-difluoro-7-[2-(dimethylaminomethyl)morpholino]-1,4-dihydro-4-oxoquinoline-3-carboxylic acid.hydrochloride in 80% yield, melting at 267°–268° C.

EXAMPLE 49 (1) A suspension of 4.1 g of ethyl 2-[4-[2-(N-ethoxycarbonyl-N-methylaminomethyl)morpholino]-2,3,5-trifluorobenzoyl]-3-cyclopropylaminoacrylate obtained by Reference example 15(2) and 1.11 g of potassium carbonate in 16 ml of dimethylformamide is stirred under heating at 55°–60° C. for 8 hours. After the reaction mixture is poured into 0 ml of ice-cold water, the obtained precipitate is collected by filtration with suction, and rinsed with water well. After washing with isopropyl ether, the precipitate is dried to give 3.23 g of ethyl 1-cyclopropyl-6,8-difluoro-7-[2-(N-ethoxycarbonyl-N-methylaminomethyl)morpholino]-1,4-dihydro-4-oxoquinoline-3carboxylate in 82% yield, melting at 122°–124° C.

NMR (CDCl$_3$), δ (ppm): 1.02–1.36 (4H, m), 1.27 (3H, t, J=7Hz), 1.40 (3H, t, J=7Hz), 3.00 (3H, s), 4.13 (2H, q, J=7Hz), 4.38 (2H, q, J=7Hz), 7.89 (1H, dd, J=13.2Hz), 8.51 (1H, s)

(2) A suspension of 2.5 g of ethyl 1-cyclopropyl-6,8-difluoro-7-[2-(N-ethoxycarbonyl-N-methylaminomethyl)morpholino]-1,4-dihydro-4-oxoquinoline-3-carboxylate in 20 ml of 10% aqueous hydrochloric acid is refluxed for 12 hours. The reaction mixture is concentrated under reduced pressure, and to the obtained crystals is added ethanol. The crystals are collected by filtration with suction, washed with ethanol and then dried to give 1.6 g of 1-cyclopropyl-6,8-difluoro-7-[2-(methylaminomethyl)morpholino]-1,4-dihydro-4-oxoquinoline-3-[carboxylic acid. hydrochloride in 73% yield, melting at 289°–290° C. with decomposition.

EXAMPLE 50

A solution of 4.93 g of ethyl 1-cyclopropyl-6,8-difluoro-7-[2-(N-ethoxycarbonyl-N-methylaminomethyl)morpholino]-1,4-dihydro-4-oxoquinoline-3-carboxylate obtained by Example 49(1), 5 ml of 18% aqueous hydrochloric acid in 50 ml of ethanol is refluxed for 7 hours. The reaction mixture is concentrated under reduced pressure, to the obtained residue is added 50 ml of chloroform and the solution is washed with water. After drying over anhydrous magnesium sulfate, the chloroform is distilled off under reduced pressure and the obtained crystals are recrystallized from a mixed solvent of ethyl acetate and isopropyl ether to give 3.53 g of 1-cyclopropyl-6,8-difluoro-7-[2-(N-ethoxycarbonyl-N-methylaminomethyl)morpholino]-1,4-dihydro-4-oxoquinoline-3-carboxylic acid in 76% yield, melting at 128°-131° C.

NMR (CDCl$_3$), δ (ppm): 1.02-1.48 (4H, m), 1.27 (3H, t, J=7Hz), 3.00 (3H, s), 4.13 (2H, q, J=7Hz), 7.87 (1H, dd, J=13.2Hz), 8.74 (1H, s)

The following compounds can be prepared in a similar manner mentioned in the above examples.

* 1-cyclopropyl-1,4-dihydro-6-fluoro-7-[2-(methylaminomethyl)morpholino]-4-oxoquinoline-3-carboxylic acid, melting at 224°-226° C.
* 7-[2-(acetylaminomethyl)morpholino]-1-cyclopropyl-6,8-difluoro-1,4-dihydro-4-oxoquinoline-3-carboxylic acid, melting at 230°-233° C.
* 6,8-difluoro-1,4-dihydro-1-(2-fluoroethyl)-7-[2-(methylaminomethyl)morpholino]-4-oxoquinoline-3-carboxylic acid, melting at 234°-235° C.
* 6,8-difluoro-1,4-dihydro-1-(2-fluoroethyl)-7-[2-(dimethyl aminomethyl)morpholino]-4-oxoquinoline-3-carboxylic acid, melting at 213°-215° C.
* 6,8-difluoro-1,4-dihydro-1-isopropyl-7-[2-(methylaminomethyl)morpholino]-4-oxoquinoline-3-carboxylic acid, melting at 231°-234° C.
* 6,8-difluoro-1,4-dihydro-1-isopropyl-7-[2-(dimethylaminomethyl)morpholino]-4-oxoquinoline-3-carboxylic acid, melting at 152°-154° C.
* 1-(4-fluorophenyl)-6,8-difluoro-1,4-dihydro-7-[2-(methylaminomethyl)morpholino]-4-oxoquinoline-3-carboxylic acid, melting at 216°-217° C. with decomposition.
* 1-(4-fluorophenyl)-6,8-difluoro-1,4-dihydro-7-[2-(dimethylaminomethyl)morpholino]-4-oxoquinoline-3-carboxylic acid, melting at 224°-225° C. with decomposition.
* 1-cyclohexyl-6,8-difluoro-1,4-dihydro-7-[2-(methylaminomethyl)morpholino]-4-oxoquinoline-3-carboxylic acid, melting at 219°-222° C.
* 1-cyclohexyl-6,8-difluoro-1,4-dihydro-7-[2-(dimethylaminomethyl)morpholino]-4-oxoquinoline-3-carboxylic acid, melting at 208°-210° C.
* 1-cyclopropyl-6,8-difluoro-1,4-dihydro-4-oxo-7-[2-(propylaminomethyl)morpholino]quinoline-3-carboxylic acid, melting at 184°-186° C.
* 1-cyclopropyl-7-[2-(cyclopropylaminomethyl)morpholino]-6,8-difluoro-1,4-dihydro-4-oxoquinoline-3-carboxylic acid, melting at 167°-171° C.

FORMULATION EXAMPLE 200 mg tablets are prepared from the following composition:

| | |
|---|---|
| Compound of Example 11 | 220 mg |
| Corn starch | 88 mg |
| Sodium carboxymethyl starch | 21 mg |
| Talc | 17.5 mg |
| Magnesium stearate | 3.5 mg |
| | 350.0 mg |

These tablets can be film-coated with 15 mg of the following composition:

| | |
|---|---|
| Hydroxypropylmethyl cellulose 2910 | 5 parts |
| Polyethylene glycol 6000 | 0.5 part |
| Talc | 1 part |
| Titanium oxide | 2 parts |
| Distilled water | 91.5 parts |

Although the present invention has been adequately discussed in the foregoing specification and examples included therein, one readily recognized that various changes and modifications may be made without departing from the spirit and scope of the present invention.

What is claimed is:

1. A quinolonecarboxylic acid compound of the formula:

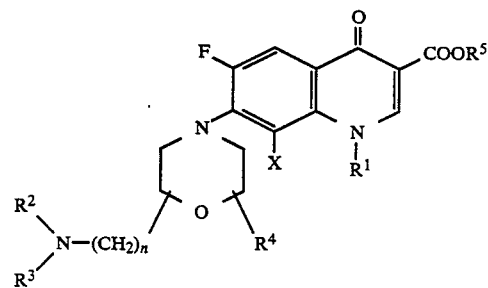

wherein $R^1$ is an alkyl group, a cycloalkyl group, a haloalkyl group, an alkenyl group, mono- or di-alkylamino groups, a phenyl group or a phenyl group substituted by one to three substituents selected from the group consisting of a halogen atom, an alkyl group, an alkoxy group, a hydroxy group, a nitro group or an amino group, $R^2$ is a hydrogen atom, an alkyl group, a cycloalkyl group, an acyl group or an alkoxycarbonyl group, $R^3$ is a hydrogen atom, an alkyl group or an aralkyl group, or $R^2$ and $R^3$ together with the adjacent nitrogen atom form a heterocyclic ring, $R^4$ is a hydrogen atom or an alkyl group, $R^5$ is a hydrogen atom, an alkyl group, an aralkyl group or an ester residue which is readily hydrolyzable in vivo, X is a hydrogen atom, a halogen atom or an alkyl group, n is an integer of 1 to 3, and a salt thereof.

2. A compound of claim 1 selected from the group consisting of 1-cyclopropyl-6,8-difluoro-1,4-dihydro-7-[2-(methylaminomethyl)morpholino]-4-oxoquinoline-3-carboxylic acid, 1-cyclopropyl-6,8-difluoro-1,4-dihydro-7-[2-(dimethylaminomethyl)morpholino]-4-oxoquinoline-3-carboxylic acid, 7-[2-(aminomethyl)morpholino]-1-cyclopropyl-6,8-difluoro-1,4-dihydro-4-oxoquinoline-3-carboxylic acid, 1-cyclopropyl-7-[2-(ethylaminomethyl)morpholino]-6,8-difluoro-1,4-dihydro-4-oxoquinoline-3-carboxylic acid, 1-cyclopropyl-7-[2-(diethylaminomethyl)morpholino]-6,8-difluoro-1,4-dihydro-4-oxoquinoline-3-carboxylic acid, 7-[2-(acetylaminomethyl)morpholino]-1-cyclopropyl-6,8-difluoro-1,4-dihydro-4-oxoquinoline-3-carboxylic acid, 1-cyclopropyl-6,8-difluoro-7-[2-(formylaminomethyl)morpholino]-6,8-difluoro-1,4-dihydro-7-[2-(morpholinomethyl)morpholino]-4-oxoquinolina-3-carboxylic acid and 1-cyclopropyl-7-[2-(cyclopropylaminomethyl)morpholino]-6,8-difluoro-1,4-dihydro-4-oxoquinoline-3-carboxylic acid.

3. A compound of claim 1 which is 1-cyclopropyl-6,8-difluoro-1,4-dihydro-7-[2-(methylaminomethyl)morpholino]-4-oxoquinoline -3-carboxylic acid.

4. A pharmaceutical composition comprising an antibacterially effective amount of the compound of claim 1 and a pharmaceutically acceptable carrier.

5. A method of treating various infectious diseases which comprises by administrating an antibacterial effective amount of the compound of claim 1.

* * * * *